(12) United States Patent
Kressner

(10) Patent No.: US 8,209,808 B2
(45) Date of Patent: Jul. 3, 2012

(54) TOOTHBRUSH AND ATTACHMENT THEREFOR

(75) Inventor: Gerhard Kressner, Altenstadt (DE)

(73) Assignee: Braun GmbH, Kronberg (DE)

( * ) Notice: Subject to any disclaimer, the term of this patent is extended or adjusted under 35 U.S.C. 154(b) by 545 days.

(21) Appl. No.: 12/520,054

(22) PCT Filed: Dec. 7, 2007

(86) PCT No.: PCT/EP2007/010674
§ 371 (c)(1),
(2), (4) Date: Jun. 18, 2009

(87) PCT Pub. No.: WO2008/074412
PCT Pub. Date: Jun. 26, 2008

(65) Prior Publication Data
US 2010/0101032 A1    Apr. 29, 2010

(30) Foreign Application Priority Data
Dec. 18, 2006  (DE) .......................... 10 2006 060 132

(51) Int. Cl.
A61C 17/34   (2006.01)
(52) U.S. Cl. ............................................. 15/28; 15/22.1
(58) Field of Classification Search ................... 15/22.1, 15/28, 22.2, 22.3, 22.4, 23, 24, 29
See application file for complete search history.

(56) References Cited

U.S. PATENT DOCUMENTS

| | | | |
|---|---|---|---|
| 4,811,445 A | 3/1989 | Lagieski et al. |
| 5,054,149 A | 10/1991 | Si-Hoe et al. |
| 5,213,434 A | 5/1993 | Hahn |
| 5,289,604 A | 3/1994 | Kressner |
| 6,367,108 B1 | 4/2002 | Fritsch et al. |
| 6,766,548 B1 | 7/2004 | Lukas et al. |
| 2004/0255409 A1 | 12/2004 | Hilscher et al. |

FOREIGN PATENT DOCUMENTS

| | | |
|---|---|---|
| DE | 42 34 764 | 5/1994 |
| DE | 195 08 932 | 9/1996 |
| DE | 297 02 508 | 6/1998 |
| DE | 103 52 993 | 6/2005 |
| EP | 0 500 537 | 11/1994 |
| EP | 1 256 327 | 12/2005 |
| WO | WO00/76420 | 12/2000 |

*Primary Examiner* — Shay Karls
(74) *Attorney, Agent, or Firm* — John P. Colbert

(57) ABSTRACT

An attachment for an electric toothbrush, including a working head and coupling member mountable on a toothbrush handpiece. The coupling member includes a sleeve-shaped coupling insert with an engagement section for locking with the handpiece. The coupling insert is displaceable relative to the coupling member or an actuating member such that an axial movement of the coupling insert relative to the coupling member or actuating member produces an unlocking/locking movement of the engagement section in a direction transverse to the attachment longitudinal direction. The attachment or actuating member is first moved axially relative to a locked coupling insert until the axial relative movement releases the lock for the coupling insert and the attachment to be separated from the toothbrush handpiece. This two-stage attaching or connecting mechanism permits use of non-self-locking connecting or faying contours because the locking movement takes place in a direction transverse to the attachment longitudinal direction.

25 Claims, 8 Drawing Sheets

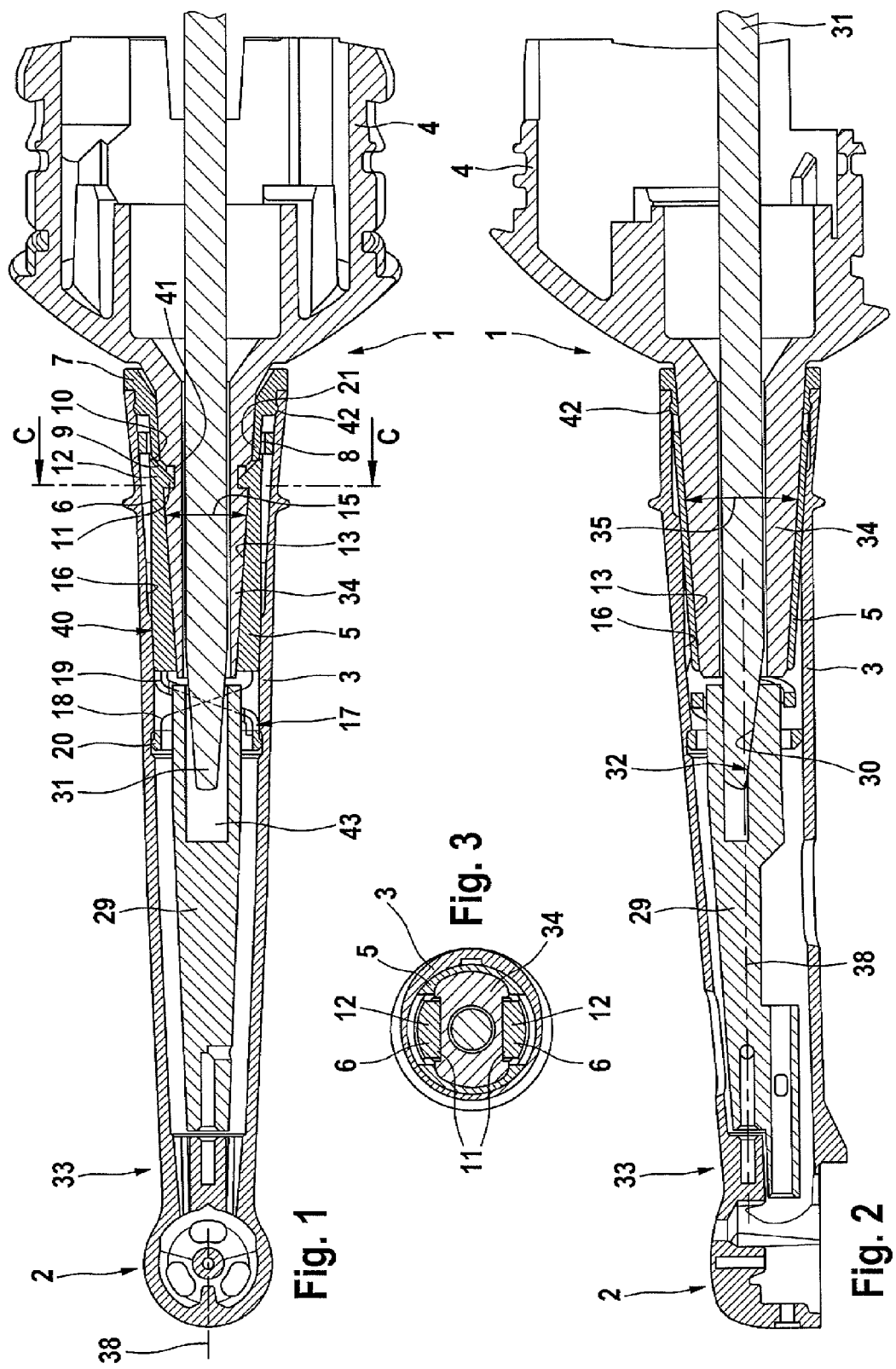

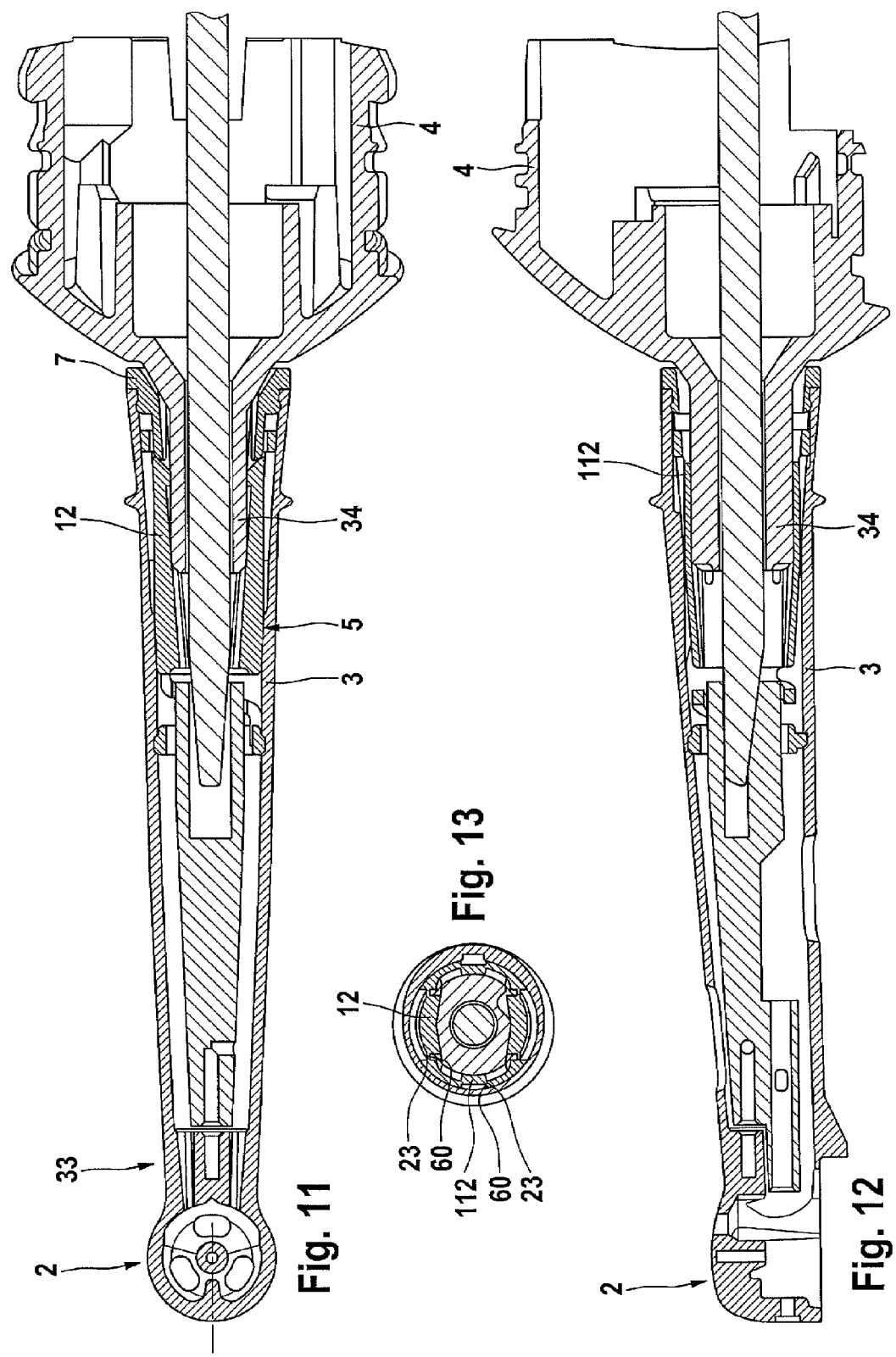

TOOTHBRUSH AND ATTACHMENT THEREFOR

TECHNICAL FIELD

This invention relates to an electric toothbrush having a handpiece and an attachment mountable thereon, and more particularly to the attachment for such a toothbrush.

BACKGROUND

EP 0 500 537 B1 discloses an electric toothbrush on which the attachment brush is connected on the one hand to a front-end shank part of the toothbrush handpiece and on the other hand to a drive shaft projecting therefrom. For this purpose, the brush has radially resilient detent hooks which can be locked in place in corresponding detent notches on the handpiece.

DE 103 52 993 A1 discloses in addition an electric toothbrush on which the attachment brush is fixed only directly to the drive shaft which projects at the front end out of the toothbrush handpiece. For this purpose the attachment brush has a coupling member with an inner recess of the blind-hole type into which an on the whole sleeve-shaped mount is inserted. Said mount, into which the drive shaft can be inserted with a snug fit, includes several spring elements which are radially resilient and intended to ensure a zero-play connection between the attachment brush and the drive shaft.

Excess play in attachment couplings and drive mechanisms can adversely affect handpiece and attachment life and performance. For example, that attachment can become separated due to the vibrations of the electric toothbrush drive and the forces applied by brushing. Accordingly, improvements are sought in electric toothbrushes and attachment tools for treating the oral cavity.

SUMMARY

One aspect of the invention features an easy-to-couple connection between the attachment and the toothbrush handpiece, which accommodates production tolerances, holds the attachment brush on the toothbrush handpiece with zero play, and yet can be readily released and re-established.

One aspect of the invention features an attachment mountable to a handpiece of an electric toothbrush. The attachment includes a working head and a coupling member joined to the working head. The coupling member is configured to be coupled to the handpiece and includes a sleeve-shaped coupling insert disposed within the coupling member. The coupling insert includes an engagement section configured to lockingly engage the handpiece. Additionally, the coupling insert is configured to be axially displaceable within the coupling member substantially along a longitudinal attachment axis to produce one of an unlocking and a locking movement of the engagement section in a direction transverse to the longitudinal attachment axis.

In some implementations, the coupling member features an actuating member including an unlocking section configured such that an axial movement of the coupling insert causes the unlocking section to engage the coupling insert and move the engagement section into an unlocked position.

In some implementations, the engagement section defines a detent contour configured to be radially movable by the actuating member.

In some implementations, the engagement section features a radially expandable detent ring axially moveable against a tapered surface on the actuating member substantially along an attachment longitudinal axis.

In some implementations, the engagement section defines a resilient catch configured to slide over the handpiece into snap-fit engagement with the handpiece.

In some cases, the catch is unseatable from snap-fitted engagement with the handpiece by an axial relative movement between the actuating member and the coupling insert.

In some implementations, the coupling insert is biased towards disengagement from the actuating member.

In some implementations, the actuating member is configured as a ring disposed in the coupling member and features actuating fingers protruding axially substantially in the attachment longitudinal direction.

In some implementations, the actuating member features a slide axially displaceable along the attachment longitudinal axis.

In some implementations, the actuating member features a ring bearing an individual attachment identifier.

In some implementations, the engagement section and an actuating member define cooperative beveled surfaces configured to cause the engagement section to move between locked and unlocked positions as the engagement section rides over the actuating member.

In some implementations, the engagement section defines a detent hook joined to a pivot arm configured such that detent hook is radially movable towards an unlocked position during axial movement of the detent contour away from the working head.

In some implementations, the coupling insert features a plurality of shell segments forming a conical mount diametrically variable through axial movement of the attachment to connect to or release the handpiece.

In some cases, the attachment features a spring biasing the shell segments towards an outwardly expanded position.

In some implementations, the coupling insert features a sleeve having an engagement section on a circumferential wall of the sleeve.

In some cases, the coupling insert features a conical mount configured to receive a complementary conical connecting member of the toothbrush handpiece push-fitted thereon.

In some cases, the conical mount of the coupling insert features a bevel of more than 7 degrees.

In some implementations, the coupling member features an insert mount configured to receive the coupling insert in an enclosed fit.

In some cases, the engagement section is radially extensible and the insert mount is substantially conical such that the coupling insert is loosely seated in the insert mount, in a position moved away from the working head.

In some cases, at least a portion of the insert mount features a cylindrical configuration.

In some implementations, the coupling insert features a spring section configured to moveably secure the coupling insert in the coupling member In some cases, the spring section features a helical spring connected to a retaining ring which is movable into engagement with an inner wall of the coupling member.

In some cases, the spring biases the coupling insert axially along an attachment longitudinal axis.

In some implementations, the at least one engagement section in an initial condition is fixed in place by means of a predetermined breaking piece in a predetermined initial position relative to the remaining body of the coupling insert. The engagement section, together with the remaining body of the coupling insert, defines a mount into which one of a cylindrical connecting member and a conical connecting member of a first toothbrush handpiece is insertable, and into which a conical connecting member of a second toothbrush handpiece is configured to be insertable by breaking the predetermined breaking piece to widen the engagement section.

In some implementations, a plug-on shaft disposed in the coupling member defines a coupling contour configured to engage a drive shaft of the toothbrush handpiece. The coupling contour further defines a conical faying surface with a bevel of more than 7 degrees.

In some cases, the coupling contour of the plug-on shaft is substantially free of undercuts or axially effective snap-action connections.

Another aspect of the invention features, an electric toothbrush with a handpiece and an attachment. The handpiece features a powered drive shaft and the attachment is configured to be driven by the drive shaft. The attachment features a working head, a coupling member joined to the working head, and a sleeve shaped coupling insert. The coupling insert is disposed within the coupling member and includes at least one engagement section configured to lock with the handpiece. Additionally, the coupling insert sleeve is configured to be axially displaceable within the coupling member substantially along a longitudinal attachment axis to produce one of an unlocking and a locking movement of the engagement section in a direction transverse to the longitudinal attachment axis.

Another aspect of the invention features an electric toothbrush including a connecting member which is insertable with a snug fit into the coupling member of an attachment brush. The coupling member is conical and has a bevel of more than 7°. The attachment includes a working head and a coupling member joined to the working head and mountable on a toothbrush handpiece. The coupling member includes a sleeve-shaped coupling insert having at least one engagement section for locking with the toothbrush handpiece by positive and/or frictional engagement therewith. The coupling insert is displaceable relative to the coupling member and/or an actuating member connected thereto axially in the attachment longitudinal direction and is connected to the engagement section, such that an axial movement of the coupling insert relative to the coupling member and/or the actuating member produces an unlocking and/or locking movement of the engagement section in a direction transverse to the attachment longitudinal direction.

Features of the device permit, between at least a part of the coupling insert and the tubular coupling member of the attachment or an engagement section joined thereto, an axial relative movement in the direction of the attachment longitudinal axis and to translate this axial relative movement into an unlocking or locking movement of the coupling insert in a direction transverse to the attachment longitudinal direction. This enables, on the one hand, a firm and also vibration-resistant connection to be obtained between the attachment and the toothbrush handpiece, while, on the other hand, enabling the connection to be released and re-established by the axial push-on and pull-off movement known in the art. The coupling insert of the attachment is displaceable relative to its coupling member and/or an actuating member connected thereto axially in the attachment longitudinal direction, and it is connected to the engagement section, which is lockable onto the handbrush handpiece by positive or frictional engagement therewith, such that an axial movement of the coupling insert relative to the coupling member and/or the actuating member produces an unlocking and/or locking movement of the engagement section in a direction transverse to the attachment longitudinal direction.

If the coupling insert or the engagement section is locked onto the toothbrush handpiece, the attachment or an actuating member connected thereto is first moved axially substantially in the attachment longitudinal direction relative to the locked coupling insert, whereby the coupling insert initially does not move relative to the toothbrush handpiece on account of its being locked thereto. After the axial relative movement has released the lock the coupling insert can be pulled together with the attachment off the toothbrush handpiece. This two-stage attaching or connecting mechanism permits even non-self-locking connecting or faying contours to be provided at the interface between the toothbrush handpiece and the coupling insert because fixedly securing is assured nevertheless by the locking movement which takes place in a direction transverse to the attachment longitudinal direction.

In particular the interface between the toothbrush handpiece and the coupling insert of the attachment can thus be rendered insensitive to tolerances, e.g., accommodating of production tolerances. On the other hand it is possible to control the axial relative movability between the coupling insert and the attachment or the actuating member fastened thereto by means of a suitable adaptation of the contour at the interface between the coupling insert and the coupling member or actuating member, in particular an unwanted axial displacement of the coupling member relative to the coupling insert can be prevented by a self-locking configuration of the contours of the coupling insert and the coupling member which are in seating engagement with each other.

In a particular implementation, the coupling insert defines a conical mount which widens away from the working head of the attachment, defining a bevel of more than 7°. The conical mount need not be configured to be self-locking, and the stub-shaped connecting member of the toothbrush handpiece, which conventionally projects at the front end, may be configured with a complementary bevel of more than 7°. These relatively pronounced tapers of the connecting member of the toothbrush handpiece and of the mount defined by the coupling insert render the connection insensitive to tolerances because differences in diameter can be compensated for by a suitable axial movement.

To avoid transferring the problem of an unwanted disengagement to the interface between the coupling insert and the coupling member of the attachment (i.e., to avoid an unwanted axial displacement of the tubular coupling member of the attachment relative to the coupling insert), which would result in unlocking of the coupling insert, it is possible to use various mechanisms. For example, other implementations provide a catch mechanism between the coupling insert and the coupling member of the attachment, which can be released by overcoming a predetermined detent force.

Alternatively or in addition, the coupling member may have an insert mount into which the coupling insert is insertable by frictional engagement with a snug and self-locking fit. For example, the insert mount may be of a conical configuration with a bevel of less than 7° so that the coupling insert firmly clamps itself in place in self-locking manner in the insert mount of the tubular coupling member when the attachment is plugged onto the toothbrush handpiece. Again, alternatively or in addition, a spring device may be provided which acts between the coupling insert and the coupling member and holds the coupling insert in the desired axial position.

To achieve simple operation of the attachment and to be able to easily pull the attachment off the toothbrush handpiece, a further aspect of the invention provides for the actuating member to have an unlocking section which is arranged and configured such that during an axial movement of the coupling insert away from the working head the unlocking section is movable into engagement with the coupling insert and forces its engagement section into an unlocked position. In other words, the actuating member is arranged and configured such that the actuating member automatically unlocks the coupling insert when the attachment is being pulled off the toothbrush handpiece.

In a particular implementation, a wedge-shaped surface is provided on the engagement section of the coupling insert and/or the actuating member, which surface produces an unlocking movement while the engagement section rides over the actuating member. A pair of wedge-shaped surfaces can be provided, but other implementations use a pair of beveled surfaces arched in a spherical or concave configuration which, while the engagement section rides over the actuating member as the result of the axial relative movement translates said axial movement into an unlocking movement in a direction transverse to the axial direction.

In reversal of the kinematics, other implementations of the invention provide for the actuating member to effect not the unlocking but the locking of the coupling insert or the engagement section connected thereto. In this case the engagement section in its initial position may adopt, or be biased into, a non-locking position. When the attachment is plugged onto the toothbrush handpiece, the engagement section of the coupling insert is forced into the locking position by way of the actuating member. Additionally, as previously described, the coupling insert may be configured to be self-locking and the locking, which occurs on its own while the attachment is being seated onto the toothbrush handpiece, is then released by means of the actuating member while the attachment is being removed again.

In a particular implementation, the engagement section forms a spring catch and/or a detent clip which, while the coupling member is being plugged onto the toothbrush handpiece, slides over its connecting member, rebounds elastically in the process and, upon reaching the fully plugged-on position, snaps into place by positive engagement. When the attachment is to be removed again from the toothbrush handpiece, the spring catch or detent clip is unseated from its snapped-in position by an axial relative movement between the actuating member and the coupling insert.

Generally, the engagement section may be configured in a variety of ways. According to particular implementation, the engagement section includes a detent contour in the form of a detent hook, which is provided on the protruding end of an engagement finger which is resilient and/or pivotal about a transverse axis and radially movable by the actuating member. Additionally, the at least one engagement finger may be integrally made of one piece with the body of the coupling insert and be separated from the rest of the body for example by longitudinal slits in order to be resilient in relation to the remaining body.

Alternatively or in addition, an engagement section may also be provided in the form of a rocker which at its one end has a detent contour in the form of a detent hook for locking engagement with the toothbrush handpiece, and at its other end forms an actuating section which is movable into engagement with the aforementioned actuating member. In this case, too, the engagement section may be integrally made of one piece with the body of the coupling insert, in particular by way of a flexible connecting bar in the middle section of the aforementioned rocker.

Alternatively or in addition, the engagement section may have a detent contour the form of a detent hook which is pivotally mounted by way of a pivot arm such that during an axial movement of the detent hook by way of the pivot arm there is produced simultaneously a radial movement component causing the detent hook to be locked or unlocked. To produce the necessary axial movement, the detent hook may have a follower element which catches the connecting member of the toothbrush handpiece while plugging on the attachment and/or the actuating member while pulling off the attachment.

According to a particular implementation, the sleeve-shaped coupling insert is provided in the form of a slotted sleeve and/or comprised of a plurality of shell segments, with the sleeve sections or the plurality of shell segments being radially extensible and compressible so that the mount defined by the sleeve sections or shell segments may adopt different diameters for accommodating the connecting member of the toothbrush handpiece. The sleeve sections or the shell segments may sit in a conical insert mount in the coupling member of the attachment so that the mount defined by the sleeve sections or shell segments is expandable or able to grow narrower or wider during axial displacement of the coupling insert in the coupling member.

A particular implementation utilizes a slotted detent ring on the whole sleeve-shaped coupling insert, which ring is diametrically variable or radially compressible and extensible. Compression may be forced by a conical seat in the coupling member or, where applicable, also by biasing the detent ring. Conversely, an extension or widening of the detent ring may be effected, for example, by way of a pair of beveled surfaces on the detent ring and the actuating member.

In a particular implementation of the invention, the coupling insert, which is axially movable in the coupling member, is fixed in place on the coupling member and secured from falling out and/or is biased into a defined initial position by means of a spring. This spring may be configured in a variety of ways. In a particular implementation, an elastic spring section is formed on the coupling insert and secured to the tubular coupling member. The elastic spring section may be formed from at least two helical and/or spiral-shaped spring arms which extend approximately on an enveloping surface, which is coaxial with the coupling insert longitudinal axis, and are connected to a retaining ring which is movable into engagement with the inner wall of the tubular coupling member, in particular by locking engagement therewith. In this arrangement, the spring may be provided on the side of the coupling insert close to the working head.

Alternatively or in addition to the axially displaceable mounting of the coupling insert in the tubular coupling member, other implementations provide an axially displaceable actuating member in the form of a slide, in order to effect the axial relative movement between the coupling insert and the actuating member. The slide may be guided, for example, in a longitudinal groove in the tubular coupling member.

In an additional implementation of the invention, the actuating member is immovably fixed in place on the tubular coupling member of the attachment. In this arrangement, the actuating member may be generally formed by an integrally formed section of the coupling member itself. In a particular implementation the actuating member is formed as a ring which is inserted in the coupling member. The actuating member may include at least one actuating finger which protrudes axially substantially in the attachment longitudinal direction and through which the coupling insert or its engagement section is actuatable in a direction transverse to the attachment longitudinal direction.

In a particular implementation of the invention, the actuating member is used in a dual function. The actuating member may have a section which is visible from the outside of the attachment and has a user-specific marking which individualizes the attachment and allows a respective user of the attachment to identify "his" or "her" attachment. The actuating member may be in the form of a colored ring of which at least portions are visible on the outside of the coupling member of the attachment, forming its front end.

In an additional implementation, the coupling insert is configured such as to enable it to be coupled with different toothbrush handpieces, to be more precise with different connecting members of such toothbrush handpieces. In particular the coupling insert is configured such as to be suitable for coupling engagement with a cylindrical connecting member of a toothbrush handpiece on the one hand and with a conical connecting member of a toothbrush handpiece on the other hand or also, where applicable, with connecting members formed with variously pronounced tapers. In an additional implementation, the at least one engagement section of the coupling insert in an initial condition is fixed in place by means of a predetermined breaking piece in a predetermined initial position relative to the remaining body of the coupling insert, such that said section defines together with said remaining body of the coupling insert a mount into which a cylindrical and/or slightly conical connecting member of a first toothbrush handpiece can be inserted with a snug fit and firmly clamped. When the at least one predetermined breaking piece is broken, the engagement section can be moved radially so that a more pronounced conical connecting member of a second toothbrush handpiece can be inserted with a snug fit with widening of the engagement section. In a particular implementation, the remaining body of the coupling insert apart from the engagement section defines a mount which is shaped to conform to the more pronounced conical connecting member of the second toothbrush handpiece.

Alternatively or in addition to providing the coupling insert with such a predetermined breaking point, the usability of the attachment on different toothbrush handpieces may be assured by the use of an adapter. In this case the coupling insert and the mount defined by it are shaped to conform to the more pronounced conical contour of the connecting member of the aforementioned second toothbrush handpiece so that such a more pronounced conical connecting member, in particular with a bevel of more than 7°, can be inserted with a snug fit. By contrast, if the attachment is to be used for an aforementioned first toothbrush handpiece having a cylindrical or only slightly conical connecting member, then a sleeve-shaped adapter whose outer contour has a more pronounced taper and is adapted in particular for a snug fit in the mount defined by the coupling insert is push-fitted onto the connecting member of said toothbrush handpiece. Such an adapter sleeve is locked by positive and/or frictional engagement on the toothbrush handpiece. The adapter sleeve may also serve to enable an attachment with a coupling insert of the aforementioned type, which includes a predetermined breaking section, to be used for a toothbrush handpiece having a cylindrical or only slightly conical connecting member even after the predetermined breaking point has been broken.

Tapers of various degrees can be used to effect self-locking of the clamp mechanism. For example, it can be advantageous in some cases to provide more pronounced complementary tapers on the stub or neck of the toothbrush handpiece and on the attachment to obtain a connection permitting more lenient tolerances.

In various cases, the attachment can be an attachment brush for dental cleansing, interproximal cleaning devices, gum massage heads or other oral care instrument.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1 is a fragmentary view, in longitudinal section, of an electric toothbrush, showing the front-end connecting member of the toothbrush handpiece and the attachment brush seated thereon, with the coupling insert seated in the tubular coupling member of the attachment brush in a locked position;

FIG. 2 is a longitudinal sectional view of the toothbrush of FIG. 1, which is turned through 90° compared to the illustration in FIG. 1;

FIG. 3 is a cross-sectional view of the toothbrush of FIGS. 1 and 2 in the region of the catch mechanism between the coupling insert in the attachment brush and the neck of the toothbrush handpiece;

FIG. 11 is a fragmentary view, in longitudinal section, of an electric toothbrush in which the coupling insert in the coupling member of the attachment brush has a predetermined breaking point and without breakage of the predetermined breaking point is suitable for a toothbrush handpiece having a cylindrical connecting member, as shown in FIG. 11, and after breakage of the predetermined breaking point is suitable for a toothbrush handpiece having a conical connecting member, with FIG. 11 showing the still unbroken condition of the predetermined breaking points;

FIG. 12 is a fragmentary view, in longitudinal section, of the toothbrush of FIG. 11 in a plane turned through 90° compared to FIG. 11;

FIG. 13 is a cross-sectional view of the connection between the attachment brush and the handpiece of the toothbrush of FIGS. 11 and 12 in the region of the detent hooks of the coupling insert.

Like reference symbols in the various drawings indicate like elements.

DETAILED DESCRIPTION

Figure 4:
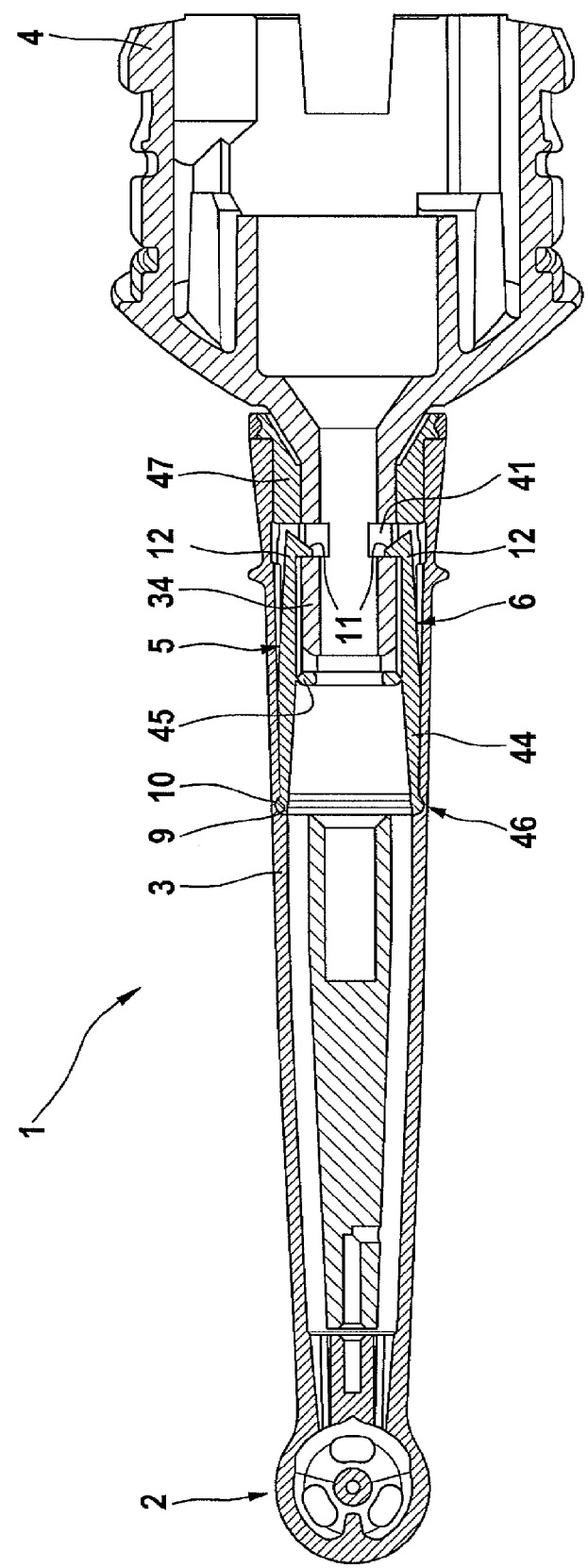
FIG. 4 is a fragmentary view, in longitudinal section, of an electric toothbrush showing the connection of the attachment brush to the handpiece of the toothbrush, with the coupling insert in the coupling member of the attachment brush including a locking rocker.

The toothbrush 1 shown in FIGS. 1 to 3 comprises a handpiece 4 and, connected thereto, an attachment in the form of an attachment brush 33. The handpiece 4 comprises a housing in which a drive motor and a power supply device are accommodated and on which an actuating switch for switching the drive on and off is provided. On the front end of the handpiece 4 shown in FIG. 1 the housing of the handpiece 4 forms a forward-protruding stub-shaped connecting member 34 which in the embodiment shown is conically shaped and tapers towards its free end, with the conical contour of the connecting member 34 advantageously having a bevel 35 of more than 7° and therefore cannot be clamped in self-locking manner. Extending from the frontal end of said connecting member 34 is a drive shaft 31 which is adapted to be driven in an oscillatory rotational motion.

The attachment brush 33 comprises a working head 2 with a set of bristles, not shown in greater detail, which, in the embodiment shown, is adapted to be driven in an oscillatory rotational motion about a bristle zone axis pointing approximately in the bristle longitudinal direction. Said working head 2 is carried by an on the whole tubular coupling member 3 which can be plugged onto the neck or the connecting member 34 of the toothbrush handpiece 4. In the interior of said tubular coupling member 3 the attachment brush 33 comprises a plug-on shaft 29 adapted to be coupled to the drive shaft 31 of the handpiece in a manner preventing relative rotation.

To fasten the attachment brush 33 to the handpiece 4 the tubular coupling member 3 includes a coupling insert 5 in the form of a coupling sleeve which is accommodated in the tubular coupling member 3 for axial displacement in the direction of the attachment longitudinal direction 38. The coupling member 3 forms with its inner wall an insert mount 16 in which the coupling insert 5 is seated with a snug fit at least in its locked condition, which will be described below in more detail. The insert mount 16 may be configured in a variety of ways, for example, it may be of an on the whole cylindrical or on the whole tapered or conical configuration, or also it may include a cylindrical section as well as a conical section. In the embodiment shown, the insert mount 16 is on the whole slightly conical, with a cylindrical section being provided on its region 40 intended for the inner end of the coupling insert 5.

A spring 17 holds the coupling insert 5 axially in the coupling member 3 or biases it into a predetermined initial position. Said spring 17 is provided on the side of the coupling insert 5 close to the working head 2. On the one hand, the spring 17 is connected to the coupling insert 5, and, on the other hand, it is fixed to the coupling member 3. In the embodiment shown, the spring 17 comprises a retaining ring 20 which is in locking engagement with the inner wall of the coupling member 3. Other implementations are possible for the spring 17. According to the illustrated implementation, the spring 17 comprises two helical or spiral-shaped spring sections 18 and 19, which coil around the plug-on shaft 29 and the drive shaft 31, cf. FIG. 1 and FIG. 2. In this arrangement, the spring sections 18 and 19 are integrally made of one piece with the coupling insert 5 and connected to the retaining ring 20. The spring 17 allows an axial movement of the coupling insert 5 to the extent required to permit locking and unlocking.

The sleeve-shaped coupling insert 5 forms with its inner circumferential surface a mount 13 which is shaped to conform to the outer circumferential contour of the connecting member 34 of the toothbrush handpiece 4 so that said handpiece can be inserted into the mount 13 with a snug fit. The mount 13 is of an on the whole conical configuration, with the bevel of the respective taper—adapted to the connecting member 34—being greater than 7°. The coupling insert 5 has two mutually opposing engagement sections 6 in the form of resilient coupling or spring fingers 12 which are integrally made of one piece with the remaining body of the coupling insert 5 and are separated from said insert by U-shaped slits so that engagement fingers 12 can spring open and shut radially in a direction transverse to the attachment longitudinal direction 38. The engagement fingers 12 extend with their longitudinal axis substantially parallel to the attachment longitudinal direction 38.

As FIG. 1 shows, the engagement fingers 12 carry on their free ends radially inwardly protruding detent hooks 11 adapted to snap into conformably shaped detent notches 41 in the outer circumferential surface of the connecting member 34 of the toothbrush handpiece 4. Other suitable detent contours may be provided; for example, a geometrical reversal of the illustrated embodiment comprising detent projections on the connecting member 34 and detent notches on the engagement fingers 12.

As FIG. 3 shows, the connecting member 34 and the mount 13 defined by the coupling insert 5 are not circular in cross section but are both flattened. In particular the connecting member 34 has two mutually opposing flattened surfaces where the detent notches 41 are provided. The engagement fingers 12 have their inner sides complementary to the two flattened surfaces and the detent notches 41 provided therein.

To be able to release the lock shown in FIG. 1 between the coupling insert 5 and the connecting member 34 of the toothbrush handpiece 4, the coupling member 3 of the attachment brush 33 includes an actuating member 7 in the form of a ring which in the illustrated embodiment is seated on the frontal end of the tubular coupling member 3 on the side remote from the working head 2. The ring may be provided as a colored ring so that it performs the dual function of individualizing the attachment brush 33 by the user being able to identify "his" or "her" attachment brush from the color of the actuating member 7.

The actuating member 7 comprises two unlocking sections 8, each in the form of an actuating finger 21 projecting axially in the attachment longitudinal direction into the interior of the coupling member 3. These actuating fingers 21 engage in the mount 13 formed by the coupling insert 5 in the area of the free ends of the engagement fingers 12. Provided on the projecting ends of the actuating fingers 21 are beveled surfaces 10 which serve to cooperate with beveled surfaces on the projecting ends of the engagement fingers 12 of the coupling insert 5. The beveled surfaces 9 and 10 are formed such that during the axial riding motion of the engagement fingers 12 over the actuating fingers 21, the engagement fingers 12 are spread radially outwardly, whereby they are lifted out of the detent notches 41 in the connecting member 34 of the toothbrush handpiece 4.

In the illustrated embodiment the coupling insert 5 is axially displaceable in the coupling member 3 in order to produce the axial movement. Alternatively or in addition, the annular actuating member 7 could be axially displaceable in the coupling member 3. In the illustrated embodiment the actuating member 7 is, however, securely seated on the coupling member 3 by a catch mechanism 42 on the inner wall of the coupling member 3.

Consequently, the following mode of operation results:

While the attachment brush 33 is being plugged onto the toothbrush handpiece 4, the connecting member 34 threads into the mount 13 of the coupling insert 5, whereby the detent hooks 11 slide along the outer circumferential surface of the connecting member 34 as the engagement fingers 12 spread open. Upon the fully plugged-on position being reached, the engagement fingers 12 spring radially inwardly causing the detent hooks 11 to engage the detent notches 41 with a snap action. The coupling insert 5 forms a spring catch which upon being plugged onto the toothbrush handpiece 4 locks automatically to said handpiece. In the locked position the connecting member 34 sits in the conical mount 13 with a snug fit. Similarly, the coupling insert 5 is snugly received in the insert mount 16 of the coupling member 3.

To release the positive-engagement lock the user simply needs to pull the attachment brush 33 in the attachment longitudinal direction 38 off the toothbrush handpiece 4. This results first in an axial relative movement between the coupling member 3 and the coupling insert 5 because the latter is held by the detent hooks 11 axially securely on the toothbrush handpiece 4. As the result of such axial relative movement the actuating fingers 21 of the actuating member 7 move under the engagement fingers 12 or the detent hooks 11 so that the engagement fingers 12 are lifted by way of the pair of beveled surfaces 9 and 10 radially out of the detent notches 41. During the axial relative movement between the coupling insert 5 and the coupling member 3, a corresponding deformation of the spring sections 18 and 19 of the spring 17 occurs.

When the engagement fingers 12 with their detent hooks 11 are unlocked from the toothbrush handpiece 4, the coupling insert 5 is pulled together with the coupling member 3 off the handpiece 4. The spring 17 operates to return the coupling insert 5 to its initial position. This spring return function is advantageous but not absolutely necessary. Due to the conical configuration of the mount 13 and/or a possibly provided follower element, the coupling insert 5 would be pushed back into its locking position when plugged again onto the toothbrush handpiece 4 even in the absence of the spring 17.

As is shown in FIG. 2, in a particular embodiment, the plug-on shaft 29 of the attachment brush 33 is coupled to the drive shaft 31 in the handpiece by conical faying surfaces, and the drive shaft 31 is conically shaped on its end protruding from the housing of the handpiece 4, a bevel being equally allowed to be greater than 7°. The plug-on shaft 29 has a conformably shaped, frontally open, advantageously blind-hole type mount 43 which comprises a faying surface 32 which is adapted to the taper of the drive shaft 31 and likewise has a bevel of more than 7°. By firmly plugging on the attachment brush 33 it is possible to obtain a connection by positive and/or frictional engagement between the plug-on shaft 29 and the drive shaft 31. This connection may be free of axially effective snap-action connections or other axial holding means.

In a particular embodiment of the invention shown in FIG. 4, the unlocking of the coupling insert 5 relative to the toothbrush handpiece 4 does not have to be effected at the free ends of the engagement fingers 12 nor by an actuating member in the form of a ring inserted at the front end. As FIG. 4 shows, the engagement sections 6 of the coupling insert 5 may be configured advantageously in the form of a rocker 44. In a manner similar to that previously described in FIGS. 1 to 3, the sleeve-shaped coupling insert 5 is provided with engagement fingers 12 which extend in the longitudinal direction, are able to spring radially outwardly and inwardly and mount detent hooks 11 on their free ends in corresponding manner. However, the engagement fingers 12 are mounted in a middle section by way of a joint 45 for pivotal movement relative to the remaining body of the sleeve-shaped coupling insert 5, whereby the joint 45 can be configured in the form of a flexible connecting section which connects said engagement fingers 12 to the remaining body of the coupling insert 5. In this arrangement, the engagement fingers 12 project axially beyond the joints 45 and have on their ends remote from the detent hooks 11 beveled surfaces 9 which cooperate with beveled surfaces 10 on the inner wall of the coupling member 3. At the same time the beveled surfaces 9 and 10 form detent means 46 by means of which the coupling insert 5 is able to make snap-action engagement with the coupling member 3. As FIG. 4 shows, the beveled surfaces 9 on the rockers 44 are part of a radial projection adapted to snap into a circumferential groove in the inner wall of the coupling member 3.

Consequently, the following mode of operation results: When it is desired to unlock the brush attachment 33 from the locked position in the toothbrush handpiece 4 shown in FIG. 4, then the attachment brush 33 is simply pulled in the attachment longitudinal direction 38 off the handpiece 4. This results first in an axial relative movement between the coupling member 3 and the coupling insert 5 because the latter is held by the detent hooks 11 securely on the toothbrush handpiece 4. As a result, the detent means 46 slide out of their engaged position, with the rockers 44 being actuated by way of the beveled surfaces 9 and 10 so that the engagement fingers 12 pivot about the joints 45 and the detent hooks 11 are levered out of the detent notches 41. After the unlocking of the detent hooks 11 the coupling insert 5 can then be pulled off together with the coupling member 3. The colored ring 47 inserted into the coupling member 3 at the frontal end prevents the coupling insert 5 from slipping completely out of the coupling member 3.

When the attachment brush 33 is plugged onto the toothbrush handpiece 4 again, first the connecting member 34 threads into the mount 13 formed by the coupling insert 5, with the detent hooks 11 sliding over the connecting member 34. As FIG. 4 shows, provision is made in the region of the joints 45 for radially inwardly protruding shoulders which form a follower element. During the plugging on, the corresponding frontal surfaces of the connecting member 34 of the handpiece 4 abut against this follower element, thus ensuring that when the plugging on is completed the coupling insert 5 is pressed fully into the coupling member 3 until the detent means 46 snap in place again on the rockers 44 and the engagement fingers 12 spring back again correspondingly in order to cause snapping engagement of the detent hooks 11 with the detent notches 41.

Figures 5, 6:
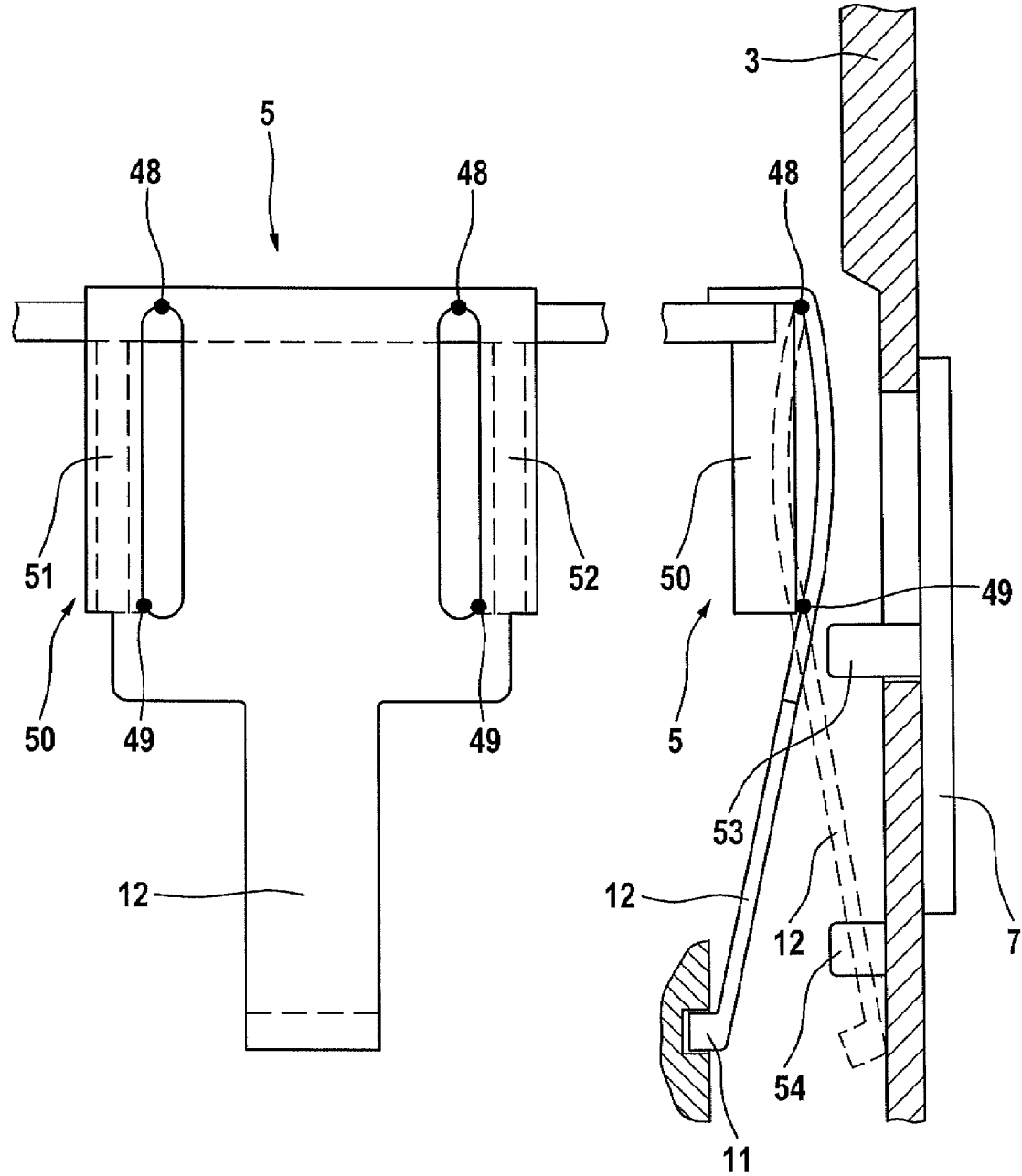
FIG. 5 is a fragmentary view, in section, of the coupling insert in the coupling member of an attachment brush, on which the coupling insert has a locking arm in the form of a bistably mounted spring finger.
FIG. 6 is a top plan view of the bistably mounted spring finger of the coupling insert of FIG. 5.

FIGS. 5 and 6 show another implementation of the invention in which the coupling insert 5 includes a bistably mounted, resilient engagement finger 12 which in accordance with the previous embodiments carries on its free end a detent hook 11 which snaps into a corresponding detent notch on the toothbrush handpiece 4. Where the embodiment shown in FIGS. 5 and 6 corresponds to the previous embodiments, reference will be made to their description.

As FIGS. 5 and 6 show, the engagement finger 12 is joined to two sections 48 and 49 spaced apart from each other in axial direction on a tension rod 50 in the form of two tension strips 51 and 52 arranged to the right and left of the engagement finger 12, such that the distance between the two attachment points on the sections 48 and 49 is shorter than the arc length of the engagement finger 12 between said two attachment points. This compels the engagement finger 12 to adopt an arcuately curved position, namely either the locked position illustrated in FIG. 5 by solid lines or the unlocked position illustrated by broken lines. The section of the engagement finger 12 between the aforementioned sections 48 and 49 forms a pressure strip. The entire arrangement corresponds, so to speak, to a "clicker" which can be pressed bistably back and forth between two positions.

To actuate the engagement finger 12 the region of the inner wall of the coupling member 3 provides an actuating member 7 with a protruding actuating lug 53 which during a corresponding axial movement is able to urge the outwardly projecting bulge of the engagement finger 12, which is in the locking position, radially inwardly in order to force the engagement finger 12 into the unlocked position. In the illustrated embodiment, the actuating member 7 is configured in the form of a slide which is axially displaceable relative to the coupling member 3. However, other implementations may provide an axially fixed actuating member 7 if required. The return to the re-locked position can be effected by a second actuating lug 54 on the inside of the coupling member 3, which acts for example on the free end section of the engagement finger 12, which faces outwards in the unlocked position, cf. FIG. 5. In this embodiment, too, the coupling insert 5, which is of a sleeve-shaped configuration and sits in the coupling member 3, may be mounted for axial displacement relative to the coupling member 3.

Figure 7:
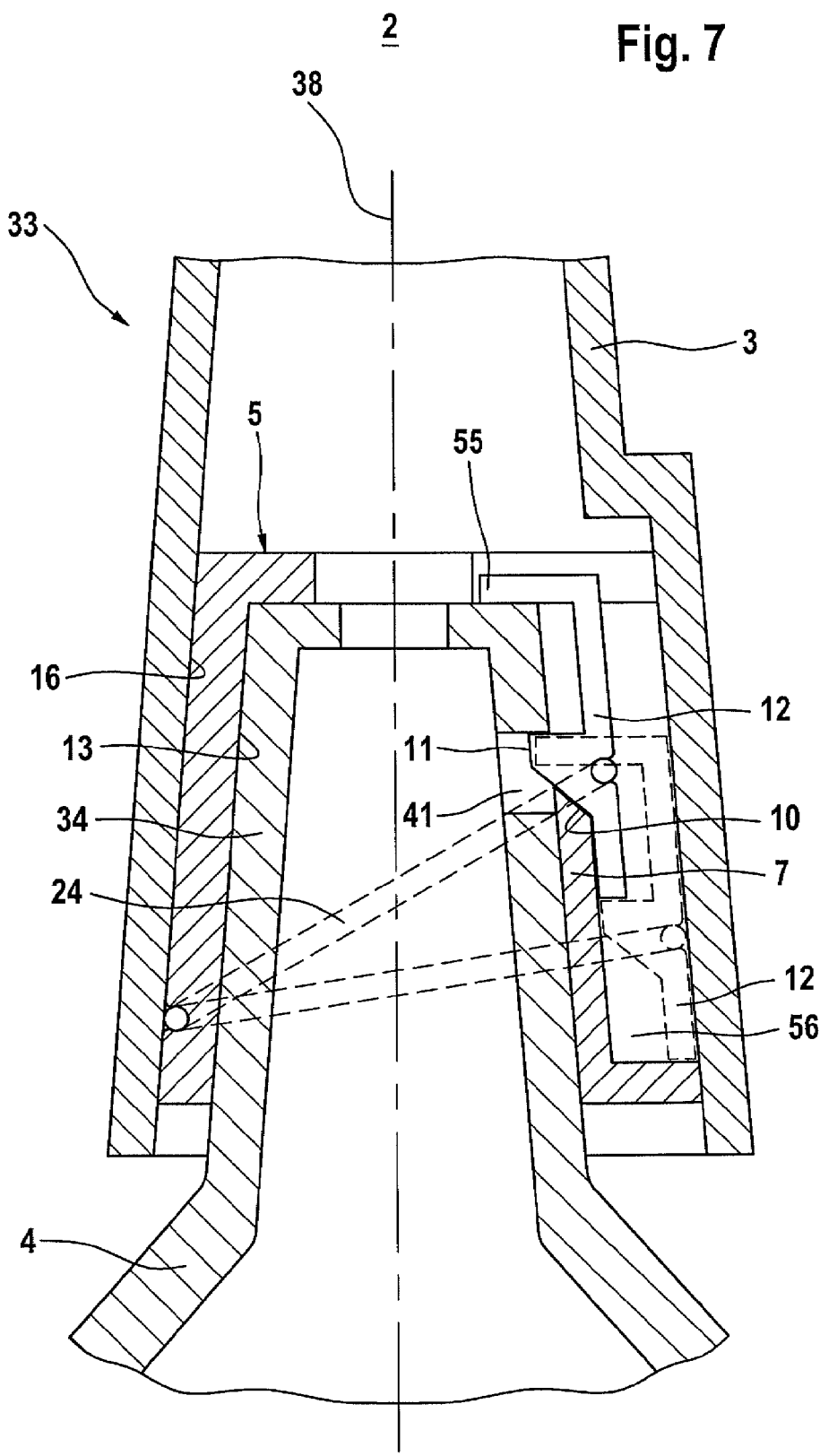
FIG. 7 is a fragmentary view, in section, of the coupling insert in the coupling member of an attachment brush in which a detent hook mounted on a pivot arm is provided.

Another implementation is shown in FIG. 7, in which the coupling insert 5 is of a sleeve-shaped configuration sitting in the coupling member 3. The insert mount 16 of the coupling member 3, in which the coupling insert 5 is seated, and/or the mount 13 of the coupling insert 5 for the toothbrush handpiece 4 may be conically formed in the previously described manner.

In the embodiment illustrated in FIG. 7, an engagement finger 12 having a radially inwardly protruding detent hook 11 is joined by way of a pivot arm 24 to the body of the coupling insert 5, such that during swinging back the engagement finger 12 is moved radially outwardly away from the working head 2, while conversely, during swinging in it is moved radially inwardly towards the working head 2. The engagement finger 12 runs in a longitudinal groove in the body of the coupling insert 5. As FIG. 7 shows, the engagement finger 12 has on its end close to the working head 2 a follower element 55 which cooperates with the frontal end of the connecting member 34 of the toothbrush handpiece 4 while the attachment brush 33 is being plugged onto the handpiece 4. When said connecting member 34 is inserted into the mount 13 of the coupling insert 5, the follower element 55 compels the engagement finger 12 to follow it and moves it axially into the recess of the coupling member 3 towards the working head 2. This forces the engagement finger 12 into its locked position, which is illustrated in FIG. 7 by solid lines. The detent hook 11 is engaged in the corresponding detent notch 41 on the toothbrush handpiece 4.

To unlock the attachment brush 33, the user simply needs to pull it in the attachment longitudinal direction 38 off the toothbrush handpiece 4. This causes the beveled surface 10 of the actuating member 7 to slide off along the beveled surface 9 of the engagement finger 12, as a result of which the engagement finger 12 is urged radially outwardly and the detent hook 11 is unlocked so that the engagement finger 12 can also be pulled off the toothbrush handpiece 4. As FIG. 7 shows, the engagement finger 12 is received in a pocket 56 between the coupling insert 5 and the coupling member 3 to enable it to travel radially outwardly a sufficient distance for disengagement from the detent notch on the toothbrush handpiece.

Figure 8:
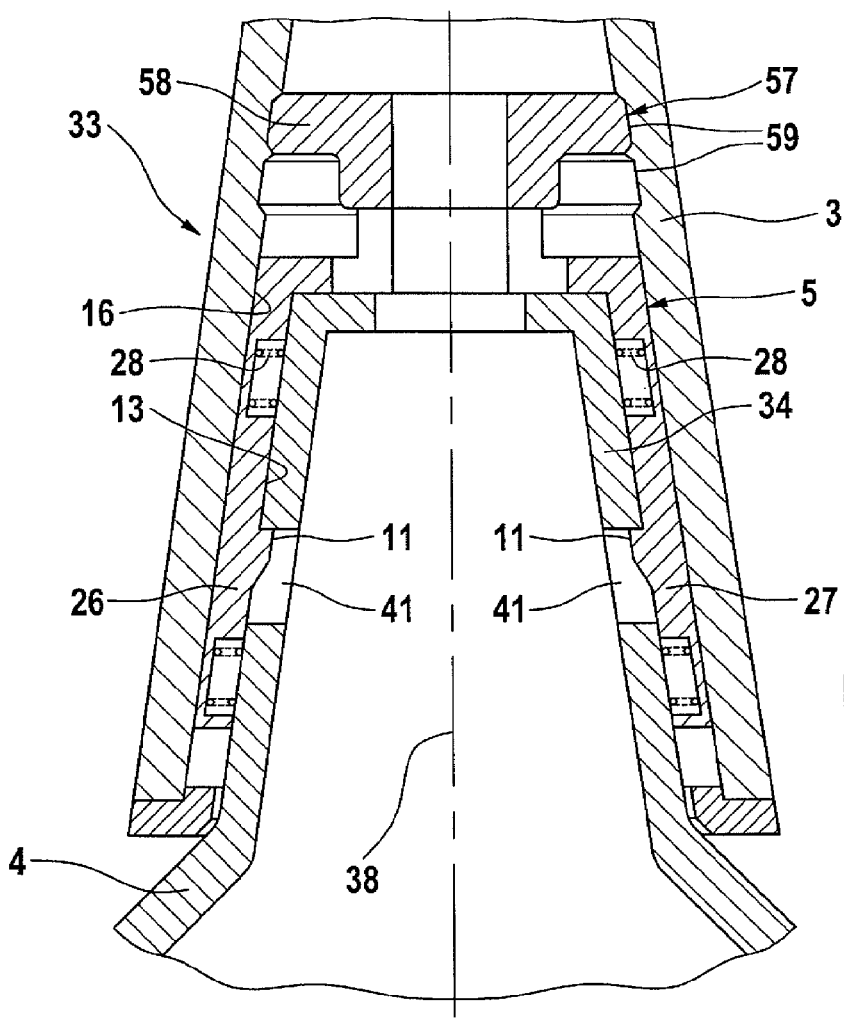
FIG. 8 is a longitudinal sectional view of the coupling insert in the coupling member of an attachment brush in which the coupling insert is in the form of a split sleeve having two shell segments.
Figure 9:
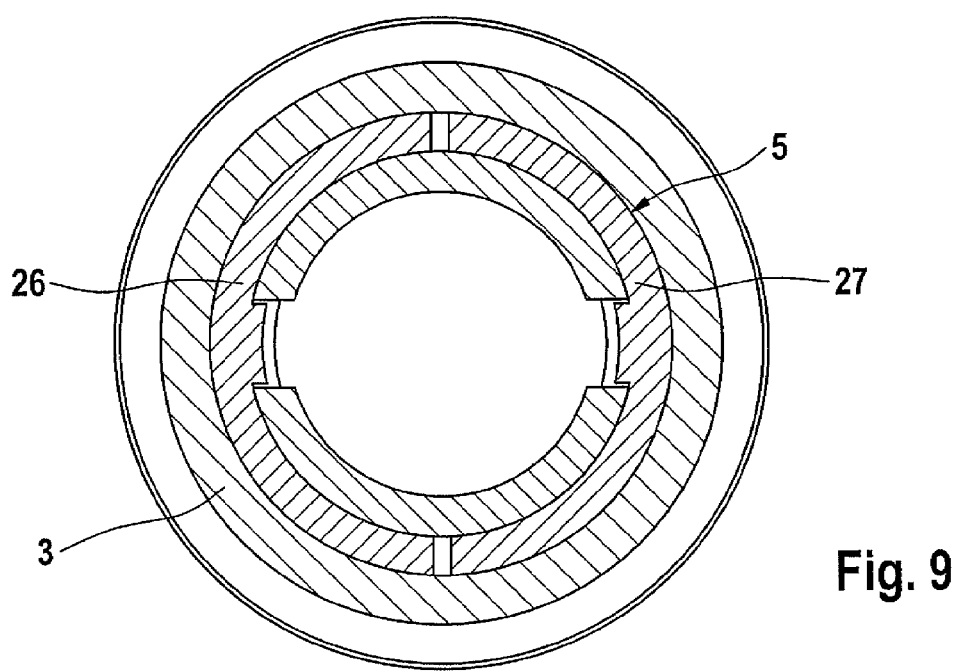
FIG. 9 is a top plan view of the coupling insert of FIG. 8, showing the two shell segments of the sleeve-shaped coupling insert.

Another embodiment of the invention is shown in FIGS. 8 and 9. In this embodiment, the coupling insert 5 has the form of a slotted sleeve so that two approximately half-shell shaped shell segments 26 and 27 define with their inner walls the mount 13 into which the connecting member 34 of the toothbrush handpiece 4 is insertable with a snug fit. FIG. 9 shows the splitting of the two shell segments 26 and 27. The two shell segments 26 and 27 are of a conical configuration on both their inner side and their outer side. The mount 13 is accordingly conical and shaped to conform to the likewise conical connecting member 34; similarly, the insert mount 16 of the coupling member 3 of the attachment brush 33 is conical.

On their inner circumferential surfaces the shell segments 26 and 27 include respective hooks 11 with which they engage the detent notches 41 on the handpiece 4 in a positive-engagement relationship.

To enable the locking and unlocking, the coupling insert 5 is mounted for axial displacement in the coupling member 3. In a particular implementation, as FIG. 8 shows, this is effected by way of a catch mechanism 57 which is movable back and forth between two axially spaced notched positions. Other mounting options may be utilized in other implementations of the invention; for example, a spring, a stick-slip seat or the like. In the embodiment shown in FIG. 8, the two shell segments 26 and 27 are fixed to a detent element 58 in the form of a detent ring which is held circumferentially in detent notches 59 on the coupling member 3. From this results the following mode of operation:

When the brush attachment 33 is to be unlocked from the locked position in the toothbrush handpiece 5 shown in FIG. 8, then the attachment brush 33 must be pulled in the attachment longitudinal direction 38 off the handpiece 4. The coupling insert 5 initially remains axially secured to the toothbrush handpiece 4 because the detent hooks 11 continue to be engaged, as the result of which an axial relative movement occurs between the coupling insert 5 and the coupling member 3. As this occurs, the detent element 58 is moved into the detent notch 59 which is a greater distance from the working head 2. Owing to this axial relative movement the coupling insert 5 obtains at the same time more radial clearance on account of the taper of the insert mount 16 so that the shell segments 26 and 27 are able to move apart in a direction transverse to the attachment longitudinal direction 38. To ensure this moving apart, for the illustrated embodiment features a spring device 28 which biases the shell segments 26 and 27 into their expanded position. In the illustrated embodiment the spring device 28 comprises spring elements which are arranged on the inner circumference of the shell segments 26 and 27 and take support upon the toothbrush handpiece 4.

When the attachment brush 33 is plugged on again, the connecting member 34 of the toothbrush handpiece 4 threads into the mount 13 until follower elements 55 on the shell segments 26 and 27 enter into engagement with the connecting member 34, as a result of which the coupling insert 5 is pressed deeper into the coupling member 3 during further insertion of the toothbrush handpiece 4. In the process, the detent element 58 is moved again into the detent notch near the coupling member 3. At the same time the shell segments 26 and 27 are caused to converge so that the hooks 11 engage again into the detent notches 41.

Figure 10:
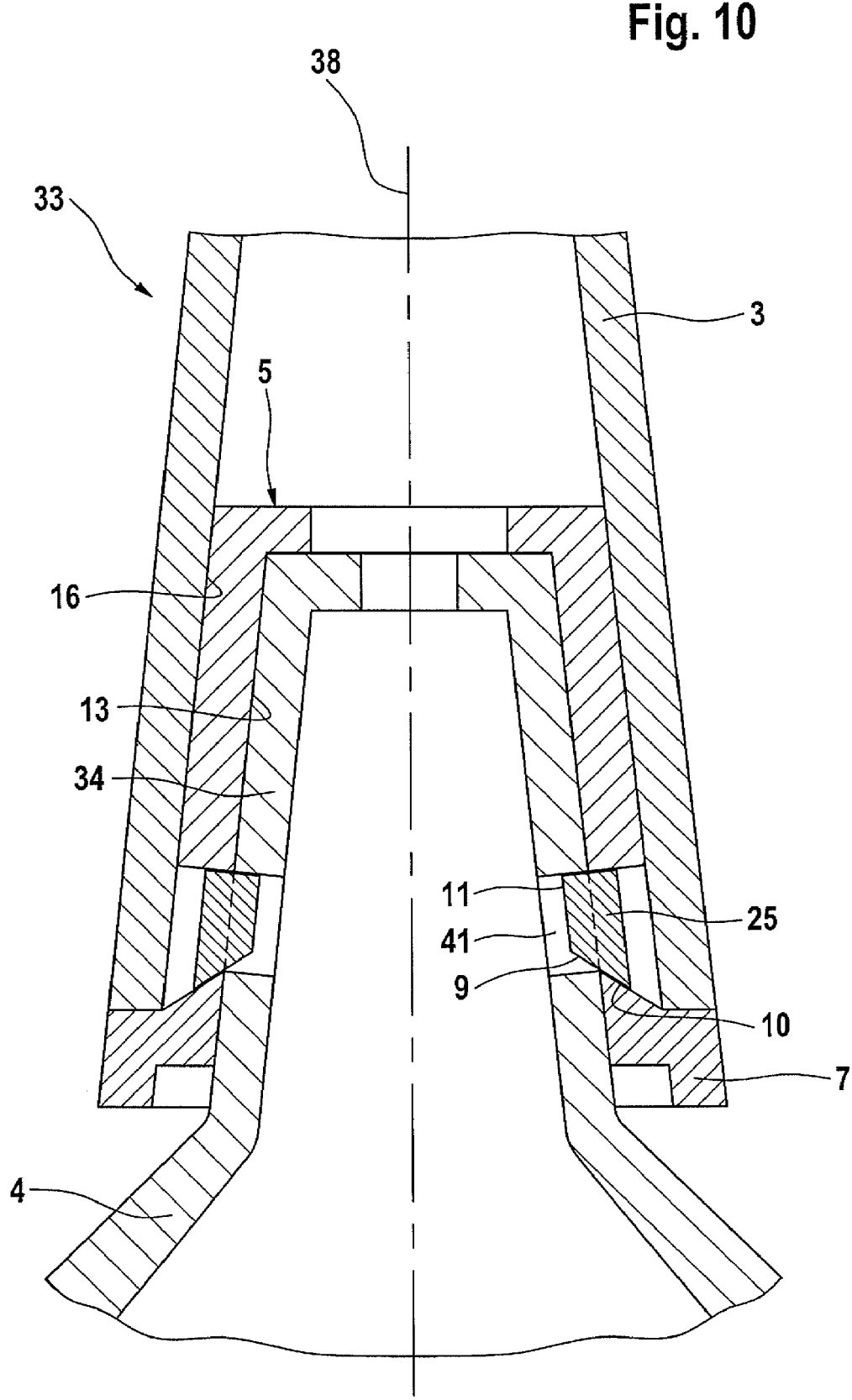
FIG. 10 is a longitudinal sectional view of the coupling insert in the coupling member of an attachment brush in which the coupling insert includes an expandable detent ring.

FIG. 10 shows a particular implementation in which the coupling insert 5 comprises a sleeve-shaped, conical body which forms with its inner side a conical mount 13 for the connecting member 34 of the toothbrush handpiece 4 and is seated with its outer side in the likewise conical insert mount 16 in the coupling member 3. In another embodiment, the body, the mount and the insert mount may be of a cylindrical rather than conical configuration. Furthermore, the coupling insert 5 includes a detent ring 25 which, on the one hand, can be radially widened and narrowed and can project relative to the inner contour of the sleeve-shaped body of the coupling insert 5. Alternatively, the detent ring 25 can be axially movable relative to the coupling member 3. In addition, it includes a beveled surface 9 which cooperates with a corresponding beveled surface 10 on the actuating member 7 which in turn is seated in the form of a ring at the frontal end of the tubular coupling member 3 where it is axially secured in place. Through axial riding of the detent ring 25 over the actuating member 7, the detent ring 25 is radially expanded by way of the pair of beveled surfaces 9 and 10, as a result of which the lock can be released. From this results the following mode of operation: When the attachment brush 33 is to be unlocked from the handpiece 4, the user needs only to pull the attachment brush 33 in the attachment longitudinal direction 38 off the toothbrush handpiece 4, whereby initially the detent ring 25 remains axially secured to the handpiece 4 as long as the detent ring 25 is in engagement with the detent notch 41. However, said ring is expanded by way of the pair of beveled surfaces 9 and 10 the further the coupling member 3 is pulled off axially until it is eventually disengaged from the detent notch 41 and can be pulled together with the coupling member 3 off the toothbrush handpiece 4. The detent ring 25 is elastically biased into its narrowed locking position; for example, in the manner of a snap ring, so that it returns on its own to its locking position. When the attachment brush 33 is plugged on again, the detent ring 25, in expanding elastically, slides over the connecting member 34 of the toothbrush handpiece 4 until it can snap into its detent notches 41.

FIGS. 11 to 14 show a particular implementation of the invention. In this implementation the coupling insert 5 is configured such that it can be plugged onto a toothbrush handpiece 4 having a more pronounced taper as well as onto a cylindrical connecting member 34 of a corresponding toothbrush handpiece 4. For this purpose the engagement fingers 12 of the coupling insert 5 are fixed in their initial condition in a position in which they protrude relative to the remaining body of the coupling insert, namely by means of predetermined breaking points or predetermined breaking pieces 23. As FIG. 13 shows, material lands 60 which bridge the U-shaped slits around the engagement fingers 12 are left standing between the sleeve-shaped body and the engagement fingers 12. The detent hooks 11 on the engagement fingers 12 are formed and arranged such that they form with their inner circumferential surface a clamping surface which can be pushed with a snug fit onto the cylindrical circumferential surface of the connecting member 34 of the toothbrush handpiece 4. Starting from the detent hooks 11, the inner circumferential contour of the engagement fingers 12 is of a slightly conical configuration so that the circumferential surface section of the connecting member 34 of the toothbrush handpiece 4, which is provided at the frontal end, can also be firmly clamped in place, cf. FIG. 11.

Figure 14:
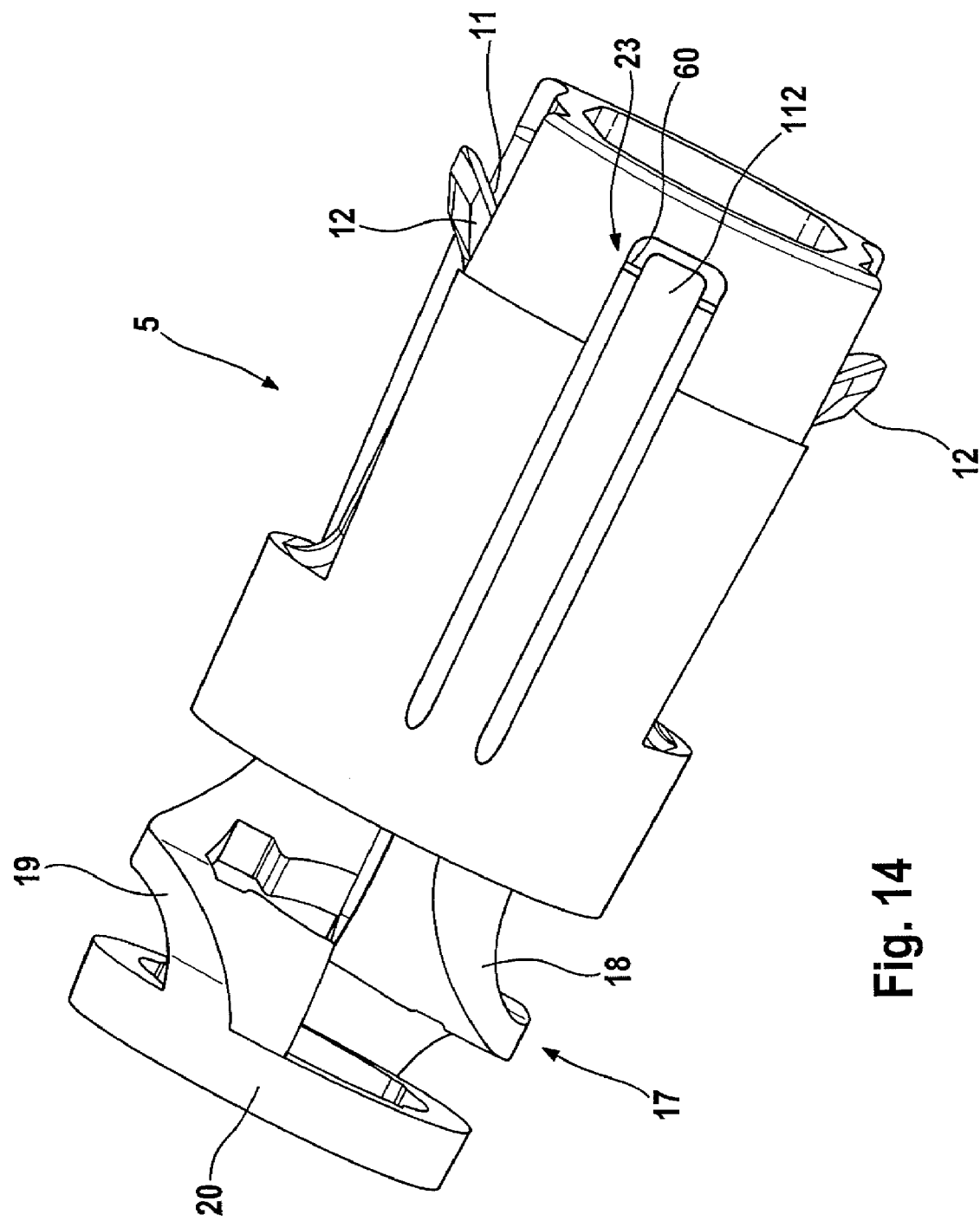
FIG. 14 is a perspective view of the coupling insert of the attachment brush of FIGS. 11 to 13.

As FIGS. 13 and 14 show, another two engagement fingers 112 are provided on the coupling insert 5, which are each offset by 90° in relation to the engagement fingers 12 and separated from said coupling insert likewise by U-shaped slits in the sleeve-shaped body of the coupling insert 5. Predetermined breaking pieces 23 are also provided in the form of material lands 60 which are left standing and force the engagement fingers 112 likewise into an inwardly protruding position, which is shown in FIG. 13. In corresponding manner these additional engagement fingers 112 define with their inner circumferential surface faying surfaces which can be pushed with a snug fit, in particular by frictional and/or clamping engagement, onto the outer cylindrical surface of the connecting member 34 of the toothbrush handpiece 4.

This particular implementation also enables the coupling insert 5 to be fixed with a snug fit on a cylindrical connecting member 14. In contrast, if the coupling insert 5 is to be pushed onto a conical connecting member 34 of a corresponding toothbrush handpiece 4, as is shown in FIGS. 1 and 2, then the predetermined breaking pieces 23 will break open, thereby enabling the engagement fingers 12 and 112 to spring outwardly, as a result of which the entire inner circumferential surface of the sleeve-shaped body of the coupling insert 5 can act as a mount 13 into which the conical connecting member of the toothbrush handpiece 4 can be inserted with a snug fit. The engagement fingers 12 then provide the catch mechanism as was described in connection with FIGS. 1 to 3.

The invention claimed is:

1. An attachment mountable to a handpiece of an electric toothbrush, the attachment comprising:
    a working head;
    a coupling member joined to the working head and configured to be coupled to the handpiece; and
    a sleeve-shaped coupling insert disposed within the coupling member and comprising an engagement section configured to lockingly engage the handpiece, wherein the coupling insert includes a spring section configured to bias the coupling insert axially within the coupling member substantially along a longitudinal attachment axis to produce one of an unlocking and a locking movement of the engagement section in a direction transverse to the longitudinal attachment axis.

2. The attachment according to claim 1 wherein the coupling member further comprises an actuating member comprising an unlocking section configured such that an axial movement of the coupling insert causes the unlocking section to engage the coupling insert and move the engagement section into an unlocked position.

3. The attachment according to claim 2 wherein the engagement section defines a detent contour configured to be radially movable by the actuating member.

4. The attachment according to claim 2 wherein the engagement section comprises a radially expandable detent ring axially moveable against a tapered surface on the actuating member substantially along an attachment longitudinal axis.

5. The attachment according to claim 2 wherein the engagement section defines a resilient catch configured to slide over the handpiece into snap-fit engagement with the handpiece.

6. The attachment according to claim 5 wherein the catch is unseatable from snap-fitted engagement with the handpiece by an axial relative movement between the actuating member and the coupling insert.

7. The attachment according to claim 2 wherein the coupling insert is biased towards disengagement from the actuating member.

8. The attachment according to claim 2 wherein the actuating member is configured as a ring disposed in the coupling member and comprising actuating fingers protruding axially substantially in the attachment longitudinal direction.

9. The attachment according to claim 2 wherein the actuating member comprises a slide axially displaceable along the attachment longitudinal axis.

10. The attachment according to claim 2 wherein the actuating member comprises a ring bearing an individual attachment identifier.

11. The attachment according to claim 1 wherein the engagement section and an actuating member define cooperative beveled surfaces configured to cause the engagement section to move between locked and unlocked positions as the engagement section rides over the actuating member.

12. The attachment according to claim 1 wherein the engagement section defines a detent hook joined to a pivot arm configured such that detent hook is radially movable towards an unlocked position during axial movement of the detent contour away from the working head.

13. The attachment according to claim 1 wherein the coupling insert comprises a plurality of shell segments forming a conical mount diametrically variable through axial movement of the attachment to connect to or release the handpiece.

14. The attachment according to claim 13 further comprising a spring biasing the shell segments towards an outwardly expanded position.

15. The attachment according to claim 1 wherein the coupling insert comprises a sleeve having an engagement section on a circumferential wall of the sleeve.

16. The attachment according to claim 15 wherein the coupling insert comprises a conical mount configured to receive a complementary conical connecting member of the toothbrush handpiece push-fitted thereon.

17. The attachment according to claim 16 wherein the conical mount of the coupling insert comprises a bevel of more than 7 degrees.

18. The attachment according to claim 1 wherein the coupling member comprises an insert mount configured to receive the coupling insert in an enclosed fit.

19. The attachment according claim 18 wherein the engagement section is radially extensible and the insert mount is substantially conical such that the coupling insert is loosely seated in the insert mount, in a position moved away from the working head.

20. The attachment according to claim 18 wherein at least a portion of the insert mount comprises a cylindrical configuration.

21. The attachment according to claim 1 wherein the spring section comprises a helical spring connected to a retaining ring which is movable into engagement with an inner wall of the coupling member.

22. The attachment according to claim 1 wherein the at least one engagement section in an initial condition is fixed in place by means of a predetermined breaking piece in a predetermined initial position relative to the remaining body of the coupling insert and defines together with the remaining body of the coupling insert a mount into which one of a cylindrical connecting member and a conical connecting member of a first toothbrush handpiece is insertable, and into which a conical connecting member of a second toothbrush handpiece is configured to be insertable by breaking the predetermined breaking piece to widen the engagement section.

23. The attachment according to claim 1 wherein a plug-on shaft disposed in the coupling member defines a coupling contour configured to engage a drive shaft of the toothbrush handpiece, said coupling contour defining a conical faying surface with a bevel of more than 7 degrees.

24. The attachment according to claim 23 wherein the coupling contour of the plug-on shaft is substantially free of undercuts or axially effective snap-action connections.

25. An electric toothbrush comprising:
a handpiece comprising a powered drive shaft; and
an attachment connectable to the handpiece and configured to be driven by the drive shaft, the attachment comprising:
a working head;
a coupling member joined to the working head; and
a sleeve shaped coupling insert disposed within the coupling member and comprising at least one engagement section configured to lock with the handpiece, wherein the coupling insert sleeve includes a spring section configured to bias the coupling insert axially within the coupling member substantially along a longitudinal attachment axis to produce one of an unlocking and a locking movement of the engagement section in a direction transverse to the longitudinal attachment axis.

* * * * *